US00PP22977P2

(12) United States Plant Patent
Ellerbrook

(10) Patent No.: US PP22,977 P2
(45) Date of Patent: Aug. 21, 2012

(54) ***BUXUS* PLANT NAMED 'SKY WALKER'**

(50) Latin Name: *Buxus sempervirens*
Varietal Denomination: Sky Walker

(76) Inventor: Mark Ellerbrook, Braverton, OR (US)

( * ) Notice: Subject to any disclaimer, the term of this patent is extended or adjusted under 35 U.S.C. 154(b) by 0 days.

(21) Appl. No.: 13/066,881

(22) Filed: Apr. 27, 2011

(51) Int. Cl.
*A01H 5/00* (2006.01)

(52) U.S. Cl. ..... Plt./226
(58) Field of Classification Search ..... Plt./226
See application file for complete search history.

*Primary Examiner* — Kent L Bell
(74) *Attorney, Agent, or Firm* — Penny J. Aguirre

(57) ABSTRACT

A new cultivar of *Buxus semperivirens*, 'Sky Walker', characterized by its very rapid growth rate that continues at least for six growing period, its very columnar plant habit with a low amount of lateral branching, its foliage with good color retention throughout the growing season, its greater degree of resistance to root diseases than is typical of *Buxus*.

2 Drawing Sheets

Botanical classification: *Buxus semperivirens*.
Variety denomination: 'Sky Walker'.

BACKGROUND OF THE INVENTION

The present invention relates to a new and distinct cultivar of *Buxus sempervirens* and will be referred to hereafter by its cultivar name, 'Sky Walker'. 'Sky Walker' is a new cultivar of boxwood grown for use as a landscape shrub.

The new cultivar was discovered by the Inventor as a naturally occurring branch mutation of an unnamed plant of *Buxus sempervirens* (not patented) that was growing in a field grown block of *Buxus Sempervirens* at a nursery in spring of 2003 in Portland, Oreg.

Asexual reproduction of the new cultivar was first accomplished by the Inventor using softwood stem cuttings in Portland, Oreg. in fall of 2004. The characteristics of 'Sky Walker' have been determined to be stable and are reproduced true to type in successive generations.

SUMMARY OF THE INVENTION

The following traits have been repeatedly observed and represent the characteristics of the new cultivar as grown outdoors in trial beds and in containers in Portland, Oreg. These attributes in combination distinguish 'Sky Walker' as a unique cultivar of *Buxus*.

1. 'Sky Walker' exhibits a very rapid growth rate; growing up to 76 cm (30 inches) in a growing season.
2. 'Sky Walker' exhibits a very columnar plant habit.
3. 'Sky Walker' exhibits little natural lateral growth.
4. 'Sky Walker' exhibits foliage with good color retention throughout the growing season.
5. 'Sky Walker' has been observed to have a greater degree of resistance to root diseases than is typical of plants of *Buxus sempervirens*.
6. 'Sky Walker' has been observed to continue its rapid growth rate at least for 6 growing seasons.

In comparison to its parent plant, 'Sky Walker' differs in having a columnar growth habit and a much faster growth rate. 'Sky Walker' can be most closely compared to other cultivars with a columnar plant habit. 'Graham Brandy' (not patented) differs from 'Sky Walker' in having a slower growth rate (12 to 15 inches less per season) and in showing less resistance to root disease. 'Monrue' (U.S. Plant Pat. No. 15,243) differs from 'Sky Walker' in having a moderate growth rate and in being freely branched with 15 to 18 lateral branches per main stem. 'Robbuxpt' (U.S. Plant Pat. No. 21,390) differs from 'Sky Walker' in having a moderate growth rate and in being densely branched. 'Furore' (U.S. Plant Pat. No. 21,319) differs from 'Sky Walker' in having a moderate growth rate, having a greater plant width, and in having numerous lateral branches.

BRIEF DESCRIPTION OF THE DRAWING

The accompanying colored photographs illustrate the overall appearance and distinct characteristics of the new *Buxus* as grown outdoors Portland, Oreg.

The photograph in FIG. 1 is a side view of 7 plants of two year-old plants (from cuttings) of 'Sky Walker' as grown in one-gallon containers.

Figure 1:
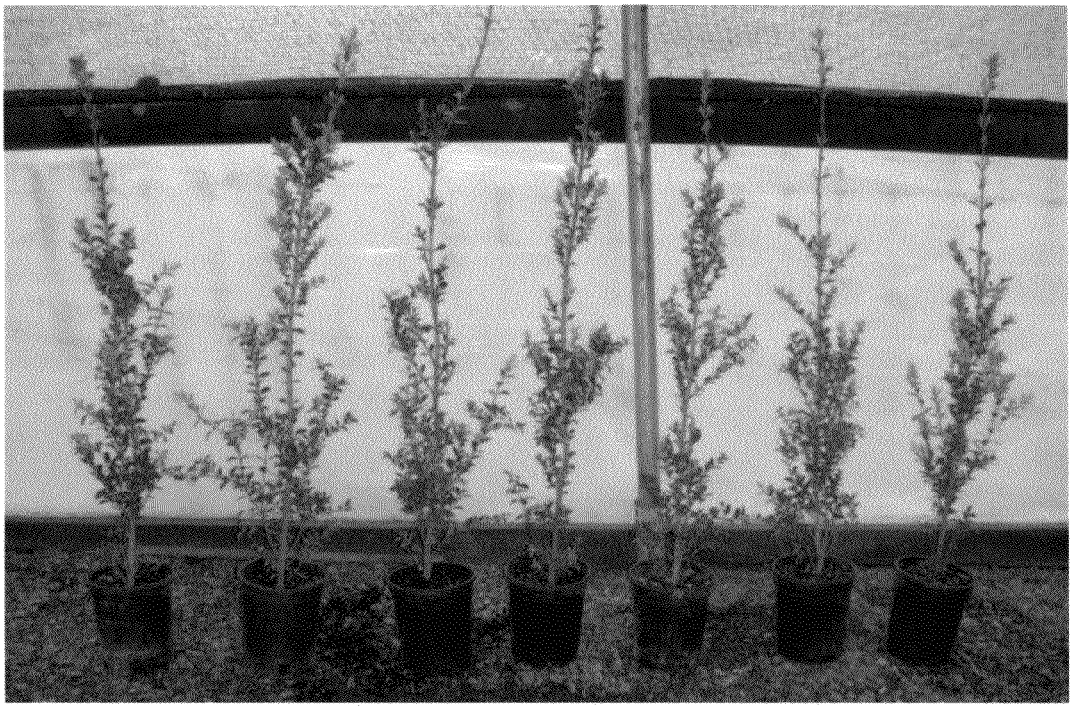
Figure 2:
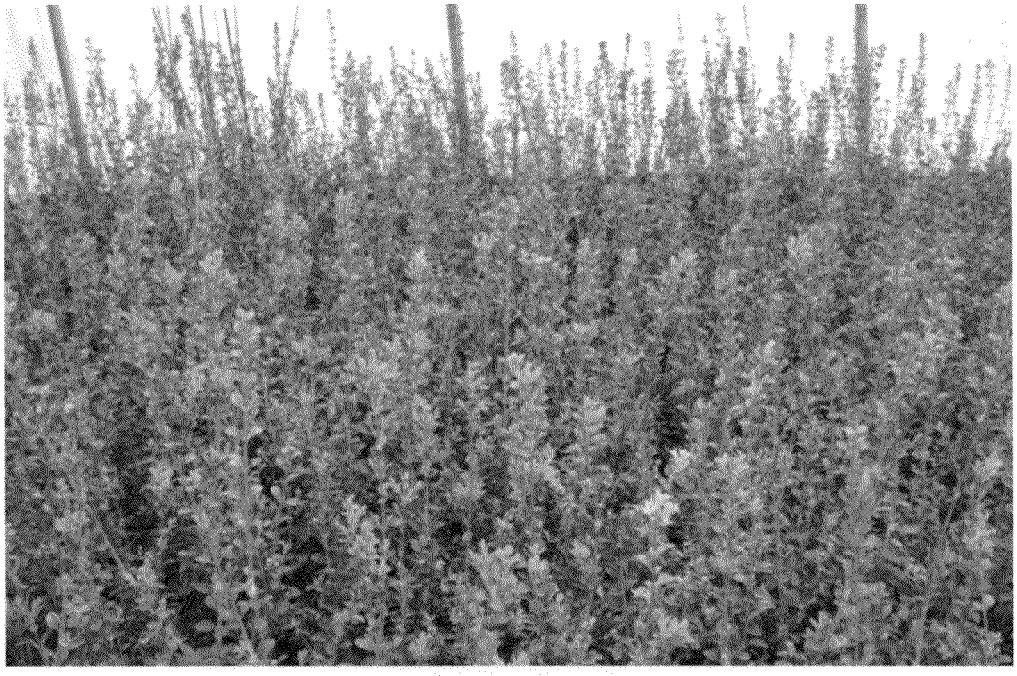

The photograph in FIG. 2 provides a view of a block of 18 month-old plants of 'Sky Walker' as grown in 4-inch containers.

Figure 3:
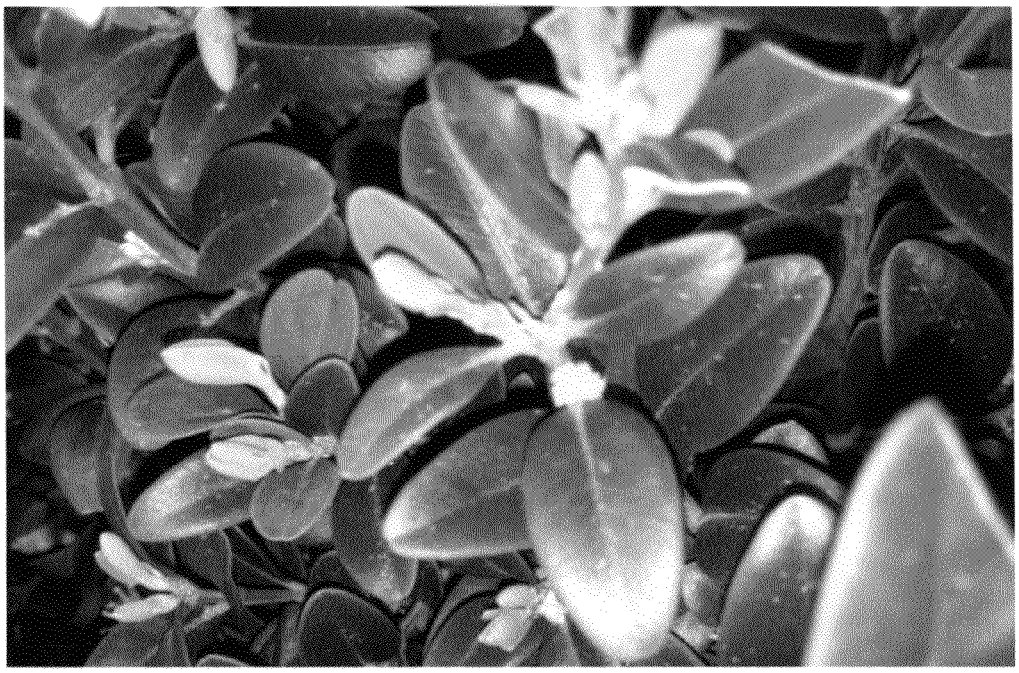

The photograph in FIG. 3 provides a close-up view of the foliage of a 6 year-old plant. The colors in the photographs may differ slightly from the color values cited in the detailed botanical description, which accurately describe the colors of the new *Buxus*.

DETAILED BOTANICAL DESCRIPTION

The following is a detailed description of 18 month-old plants of the new cultivar as grown outdoors in 4-inch containers in Portland, Oreg. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Evergreen, perennial shrub.

*Plant habit*.—Compact, upright, columnar.

*Height and spread*.—Reaches about 1.8 m (6 feet) in height and 30 to 38 cm (12 to 15 inches) in width in 6 years, an average of 76 cm in height 13 cm in width as grown in a 4-inch container.

*Cold hardiness*.—U.S.D.A. Zones 6 to 8.

*Diseases resistance*.—Has shown resistance to root disease.

*Root description*.—Fibrous.

Growth and propagation:

*Propagation*.—Softwood stem cuttings.

*Growth rate*.—Very vigorous relative to other boxwood cultivars, can grow up to 24 to 30 inches in a season.

Stem description:

*Shape*.—Quadrangular.

*Stem color*.—New growth; a blend of 144A and 144B, mature bark; 161B with vertical ridges of 191A.

*Stem size*.—An average about 76 cm in length and 5 mm in width (4 inch pot).

*Stem surface*.—Lightly pubescent prior to bark formation.

*Main branching*.—Stems arise from base, limited lateral branching unless pinched, an average 4 lateral branches as grown in a 4-inch container: An average of 20 cm in length and 3 mm in width, internode length is an average of 7 cm, a blend of 144A and 144B in color, lightly pubescent surface.

Foliage description:

*Leaf shape*.—Elliptic.

*Leaf division*.—Simple.

*Leaf base*.—Cuneate.

*Leaf apex*.—Retuse.

*Leaf fragrance*.—None.

*Leaf venation*.—Pinnate, midrib is conspicuous on lower surface only, matches leaf color on upper surface, 138C in color on lower surface.

*Leaf margins*.—Entire.

*Leaf arrangement*.—Opposite.

*Leaf attachment*.—Petiolate.

*Leaf internode length*.—Average of 3.5 cm.

*Leaf surface*.—Glabrous and satiny on upper and lower surface, coriaceous in texture.

*Leaf size*.—An average of 3.5 cm in length and 2 cm in width when mature.

*Leaf quantity*.—Average of 20 on a branch 20 cm in length.

*Leaf color*.—Newly expanded leaves; upper surface a blend of 144A and 144B, lower surface; 144B, mature leaves; upper surface N137A, lower surface a blend of 138A and 144A.

*Petioles*.—An average of 4 mm in length and 1.5 mm in width to stem and sheathed to lower node, color 138B on up per surface and 138C on lower surface, glabrous surface.

*Stipules*.—An average of 4 mm in length and 2 mm in width and 138B in color, develop into small leaves similar in characteristics to main leaves.

Inflorescence description:

*Significance*.—Flowers are insignificant and non-showy.

*Blooming period*.—For about 2 weeks in April in Oregon.

*Inflorescence type*.—Monoecious, Axillary tight rounded clusters of a single female flowers surrounded by about 6 male flowers.

*Inflorescence size*.—About 8 cm in length and width.

*Lastingness of inflorescence*.—About one week.

*Inflorescence fragrance*.—Slightly fragrant.

*Male flowers*.—About 3 cm in width and height, tepals; 4, about 2 cm in width and in length, glabrous surface, sessile to node, cuneate base and apex, 145C in color.

*Female flower*.—About 3 cm in width and length, tepals; about 4, about 2 cm in length and width, glabrous surface, cuneate apex and base, 145C in color.

*Reproduction organs*.—Stamens; 4, conspicuous and emerge from a pistillode (about 1 cm in diameter and 145C in color), filament is about 1 cm in length and 145D in color, anthers are about 1 cm in length and 9A in color, pollen was not observed. Pistils; 1, stigmas 3 and 145D in color, filaments 145C in color, ovary 145B in color and about 1 cm in length and 0.75 cm in width.

*Fruit and seed*.—Fruit; ovoid in shape, 3-valved with short horns at apex, about 7 mm in length and 6 mm in width, 137C in color, dehiscing into capsules, seed; 2 per capsule, oblong in shape, about 3 mm in length and 1 mm in width, shiny surface, 202A in color.

It is claimed:

1. A new and distinct cultivar of *Buxus* plant named 'Sky Walker' as herein illustrated and described.

* * * * *